United States Patent
Maxwell et al.

(10) Patent No.: US 11,580,945 B2
(45) Date of Patent: *Feb. 14, 2023

(54) CONFINEMENT OR MOVEMENT OF AN OBJECT USING FOCUSED ULTRASOUND WAVES TO GENERATE AN ULTRASOUND INTENSITY WELL

(71) Applicant: University of Washington, Seattle, WA (US)

(72) Inventors: Adam D. Maxwell, Seattle, WA (US); Oleg A. Sapozhnikov, Seattle, WA (US); Wayne Kreider, Seattle, WA (US); Michael R. Bailey, Seattle, WA (US)

(73) Assignee: University of Washington, Seattle, WA (US)

( * ) Notice: Subject to any disclaimer, the term of this patent is extended or adjusted under 35 U.S.C. 154(b) by 504 days.

This patent is subject to a terminal disclaimer.

(21) Appl. No.: 16/740,320

(22) Filed: Jan. 10, 2020

(65) Prior Publication Data
US 2020/0227018 A1 Jul. 16, 2020

Related U.S. Application Data

(63) Continuation of application No. 15/508,841, filed as application No. PCT/US2015/046875 on Aug. 26, 2015, now Pat. No. 10,535,332.

(Continued)

(51) Int. Cl.
*G10K 11/18* (2006.01)
*G10K 11/26* (2006.01)
(Continued)

(52) U.S. Cl.
CPC .......... *G10K 11/008* (2013.01); *A61B 17/225* (2013.01); *A61B 17/2255* (2013.01);
(Continued)

(58) Field of Classification Search
CPC ...... G10K 11/008; G10K 11/20; G10K 11/30; G10K 11/346; G10K 11/34; G10K 11/24;
(Continued)

(56) References Cited

U.S. PATENT DOCUMENTS

| 4,749,900 A | 6/1988 | Hadimioglu et al. |
| 6,029,518 A * | 2/2000 | Oeftering ........... B01D 19/0078 |
| | | 73/570.5 |

(Continued)

FOREIGN PATENT DOCUMENTS

| JP | 2013-527782 A | 7/2013 |
| WO | 2011/133922 A2 | 10/2011 |
| WO | 2013/140175 A1 | 9/2013 |

OTHER PUBLICATIONS

Second Chinese Office Action, dated Aug. 12, 2020, issued in corresponding Chinese Application No. 201580058213.2, filed Aug. 26, 2015, 9 pages.

(Continued)

*Primary Examiner* — Edgardo San Martin
(74) *Attorney, Agent, or Firm* — COJK/University of Washington

(57) ABSTRACT

A method includes transmitting a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure. The method further includes confining an object within the ultrasound intensity well. Additionally, an acoustic lens is configured to be acoustically coupled to an acoustic transducer. The acoustic lens has a varying longitudinal thickness that increases proportionally with respect to increasing azimuth angle of the acoustic lens. Another acoustic lens is configured to be acoustically coupled to an (Continued)

acoustic transducer. The acoustic lens includes a plurality of segments. Each of the plurality of segments has a varying longitudinal thickness that increases proportionally with respect to increasing azimuth angle of the segment.

22 Claims, 11 Drawing Sheets

Related U.S. Application Data

(60) Provisional application No. 62/046,654, filed on Sep. 5, 2014.

(51) Int. Cl.

| | | |
|---|---|---|
| *A61B 17/225* | (2006.01) | |
| *G10K 11/00* | (2006.01) | |
| *G10K 11/30* | (2006.01) | |
| *G10K 15/00* | (2006.01) | |
| *G10K 11/34* | (2006.01) | |
| *G10K 11/20* | (2006.01) | |
| *G10K 11/24* | (2006.01) | |
| *H03H 9/64* | (2006.01) | |
| *A61B 17/22* | (2006.01) | |

(52) U.S. Cl.
CPC .............. *G10K 11/20* (2013.01); *G10K 11/24* (2013.01); *G10K 11/30* (2013.01); *G10K 11/346* (2013.01); *G10K 15/00* (2013.01); *H03H 9/6483* (2013.01); *A61B 2017/22028* (2013.01)

(58) Field of Classification Search
CPC ...... G10K 11/002; G10K 11/26; G10K 11/18; G10K 15/00; A61B 17/225; A61B 17/2255; A61B 2017/22028; A61B 2017/22027; A61B 2017/22004; H03H 9/6483

See application file for complete search history.

(56) References Cited

U.S. PATENT DOCUMENTS

| | | | | |
|---|---|---|---|---|
| 6,055,859 | A * | 5/2000 | Kozuka | B01J 19/0093 |
| | | | | 210/748.05 |
| 6,216,538 | B1 * | 4/2001 | Yasuda | G10K 15/00 |
| | | | | 73/570.5 |
| 6,537,220 | B1 * | 3/2003 | Friemel | G01S 15/8927 |
| | | | | 600/447 |
| 6,719,449 | B1 * | 4/2004 | Laugharn, Jr. | B01F 35/2115 |
| | | | | 366/127 |
| 8,523,774 | B2 * | 9/2013 | Yen | G01S 7/5202 |
| | | | | 600/443 |
| 10,535,332 | B2 * | 1/2020 | Maxwell | H03H 9/6483 |
| 10,780,298 | B2 * | 9/2020 | Cain | A61N 7/00 |
| 2003/0055308 | A1 | 3/2003 | Friemel et al. | |
| 2011/0033922 | A1 | 2/2011 | Landers et al. | |
| 2011/0060226 | A1 | 3/2011 | Yen et al. | |
| 2013/0047728 | A1 | 2/2013 | Cochran et al. | |

OTHER PUBLICATIONS

International Search Report and Written Opinion dated Jan. 6, 2016, issued in corresponding International Application No. PCT/US15/46875, filed Aug. 26, 2015, 14 pages.

International Preliminary Report on Patentability and Written Opinion dated Mar. 16, 2017, issued in corresponding International Application No. PCT/US2015/046875, filed Aug. 26, 2015, 12 pages.

Bailey, M.R., et al., "Vortex Beams and Radiation Torque for Kidney Stone Management," Journal of the Acoustical Society of America 139(4):2040, Apr. 2016 [1-page abstract].

Sapozhnikov, O., et al., "Design and Characterization of a 2-Dimensional Focused 1.5-MHz Ultrasound Array With a Compact Spiral Arrangement of 256 Circular Elements," presentation, Proceedings of the IEEE International Ultrasonics Symposium (IUS), Tours, France, Sep. 18-21, 2016, 1 page.

Sapozhnikov, O., et al., "Rotating Small Solid Objects in Liquids by a Focused Vortex Ultrasound Beam," presentation, Proceedings of the 20th International Symposium on Nonlinear Acoustics (ISNA 2015), Lyon, France, Jun. 29-Jul. 3, 2015, 1 page.

Sapozhnikov, O., et al., "Solid Particle Transverse Trapping at the Focus of 1.5-MHz Vortex Beam Radiated by 12-Sector Ultrasonic Array," presentation, Proceedings of the IEEE International Ultrasonics Symposium (UFFC 2014), Chicago, Sep. 3-6, 2014, 1 page.

Sapozhnikov, O.A., et al., "Radiation Force of a Focused Ultrasound Beam to Reposition Small Solid Objects in Application to Kidney Stone Disease," presentation, International Congress on Ultrasonics (ICU 2015), Metz, France, May 10-15, 2015, 1 page.

Third Joint Meeting of the Acoustical Society of America and the European Acoustics Association Acoustics '17 Boston), Journal of the Acoustical Society of America, Boston, Jun. 25-29, 2017, 2 pages.

Communication Pursuant to Rule 164(1) EPC dated Mar. 21, 2018, issued in corresponding European Application No. 15837327.4, filed Aug. 26, 2015, 14 pages.

Notification of Reasons for Refusal, dated Mar. 28, 2018, issued in Japanese Application No. 2017-531964, filed Aug. 26, 2015, 7 pages.

Extended European Search Report, dated Jun. 26, 2018, issued in European Application No. 15837327.4, filed Aug. 26, 2015, 12 pages.

First Office Action, dated Feb. 6, issued in related Chinese Application No. 201580058213.2, filed Aug. 26, 2015, 18 pages.

\* cited by examiner

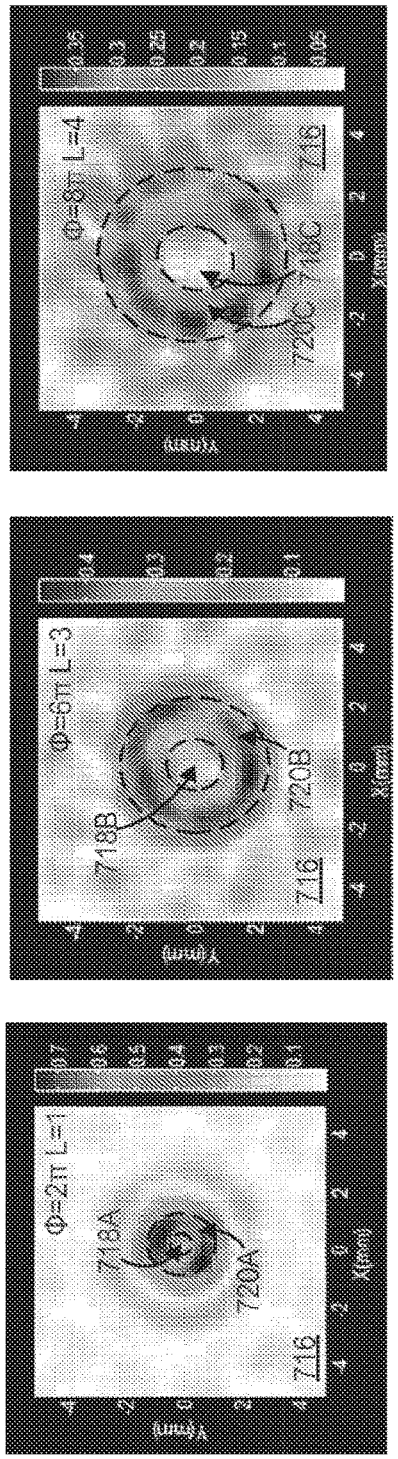
FIG. 7A
FIG. 7B
FIG. 7C
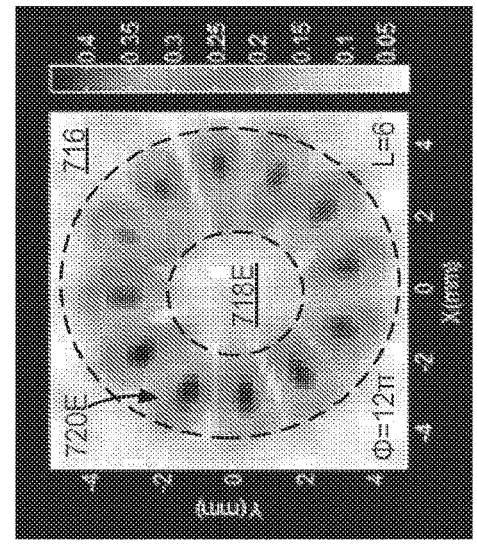
FIG. 7E
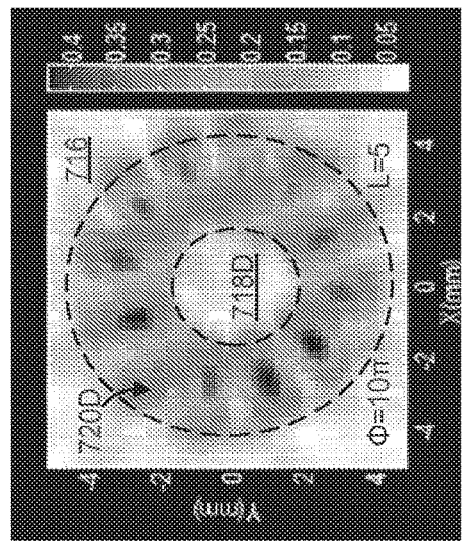
FIG. 7D

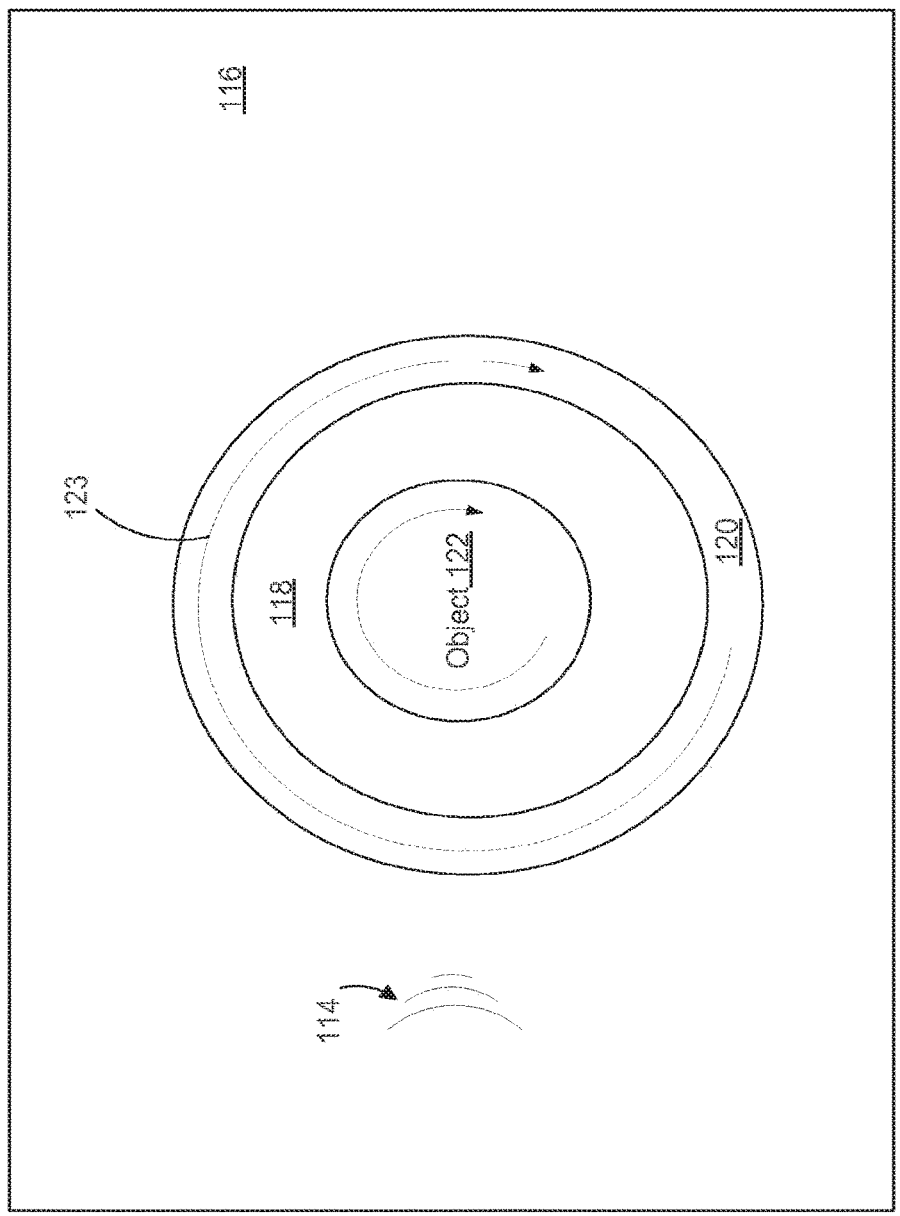

CONFINEMENT OR MOVEMENT OF AN OBJECT USING FOCUSED ULTRASOUND WAVES TO GENERATE AN ULTRASOUND INTENSITY WELL

CROSS-REFERENCE TO RELATED APPLICATION

This application is a continuation of U.S. patent application Ser. No. 15/508,841, filed Mar. 3, 2017, now U.S. Pat. No. 10,535,332, which is a national phase application under Sec. 371 of International Application No. PCT/US2015/046875, filed Aug. 26, 2015, which claims the benefit of U.S. Provisional Patent Application No. 62/046,654, filed on Sep. 5, 2014, the contents of which are incorporated herein by reference in their entirety.

STATEMENT REGARDING FEDERALLY SPONSORED RESEARCH OR DEVELOPMENT

This invention was made with government support under Grant Nos. 1R01 DK092197-02, 2P01 DK043881-15, 2R01 EB007643-05, and 2T32 DK007779-11A1, awarded by the National Institutes of Health. The government has certain rights in the invention.

BACKGROUND

Unless otherwise indicated herein, the materials described in this section are not prior art to the claims in this application and are not admitted to be prior art by inclusion in this section.

Previously known methods using ultrasound waves to acoustically confine or move an object are ineffective in moving or confining some objects. For instance, these methods are not well suited for moving or confining a large object, an object with a high mass density, or an object through which acoustic waves travel at a high rate of speed, such as a kidney stone.

SUMMARY

An example method includes transmitting a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure. The method further includes confining an object within the ultrasound intensity well.

An example acoustic lens is configured to be acoustically coupled to an acoustic transducer. The acoustic lens has a varying longitudinal thickness that increases proportionally with respect to increasing azimuth angle of the acoustic lens.

Another example acoustic lens is configured to be acoustically coupled to an acoustic transducer. The acoustic lens includes a plurality of segments. Each of the plurality of segments has a varying longitudinal thickness that increases proportionally with respect to increasing azimuth angle of the segment.

An example device includes an acoustic transducer, one or more processors, and a computer-readable medium. The computer-readable medium stores instructions that, when executed by the one or more processors, cause the acoustic transducer to perform functions. The functions include transmitting a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure. The functions further include confining an object within the ultrasound intensity well.

An example computer-readable medium stores instructions that, when executed by a computing device comprising an acoustic transducer and/or an acoustic lens, cause the acoustic transducer and/or the acoustic lens to perform functions. The functions include transmitting a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure. The functions further include confining an object within the ultrasound intensity well.

When the term "substantially" or "about" is used herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. In some examples disclosed herein, "substantially" or "about" means within +/−5% of the recited value.

As used herein, the term "ultrasound" may generally refer to frequencies of acoustic waves that are higher than the range of frequencies typically perceptible by humans (e.g., 20 Hz-20 kHz), but this term should not be interpreted as excluding embodiments that include acoustic waves with frequencies that fall within the range of frequencies typically perceptible by humans.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 7A, 7B, 7C, 7D, and 7E show measured pressure amplitudes within a focal plane of a medium for various values of L.

FIG. 10 shows rotation of an example object via a mechanical torque provided by an ultrasound wave.

DETAILED DESCRIPTION

Figure 1:
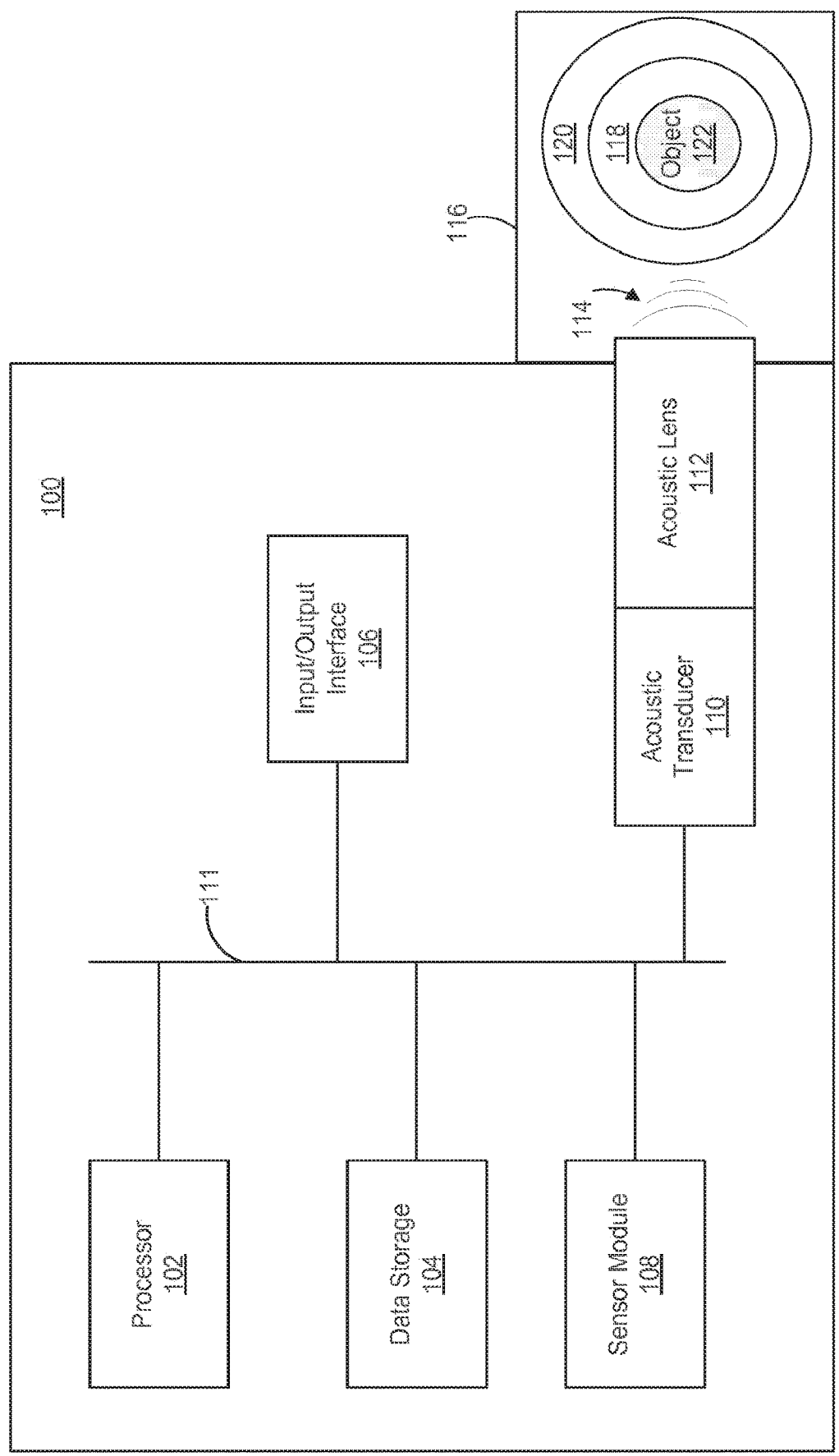
FIG. 1 is a simplified block diagram of an example acoustic transducer device.

As noted above, previously known methods using ultrasound waves to move or confine objects are ineffective for objects of large size or high mass density. The methods and systems disclosed herein are suitable for moving or confining objects that are larger and/or denser than the objects that can be confined or moved using previously known methods. For example, an acoustic transducer may transmit a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure. In some examples, the ultrasound intensity well may take on a somewhat circular shape that is defined by the surrounding region of the medium. By forming the ultrasound intensity well around an object or by steering a pre-formed ultrasound intensity well so as to surround the object, the object may be confined within the ultrasound intensity well. The ultrasound intensity well may also be steered (mechanically and/or electronically) to move the object within the medium. More specifically, the object may be moved in directions transverse to the propagation direction of the ultrasound wave.

In one example, a progressive phase shift is imparted to the ultrasound wave via the acoustic transducer. The acoustic transducer may include m (piezoelectric) transducer elements arranged in a circular pattern. Each of the m transducer elements may transmit a respective component of the ultrasound wave that is phase shifted by $2\pi L/m$ radians with respect to a component of the ultrasound wave transmitted by an adjacent transducer element. L may be a nonzero integer and m may be greater than or equal to 3, for example. Input signals representing the various phase-shifted components of the ultrasound wave may be provided to the respective transducer elements via a signal generator, for example. In this way, the progressive phase shift is imparted to the ultrasound wave with respect to an azimuth angle of the acoustic transducer from which the various components of the acoustic wave are transmitted, resulting in the formation of the ultrasound intensity well. The diameter of the ultrasound intensity well may be increased by (electronically) increasing the magnitude of L and decreased by (electronically) decreasing the magnitude of L.

In another example, the progressive phase shift is imparted to the ultrasound wave via a first acoustic lens. The first acoustic lens may have a varying longitudinal thickness that increases proportionally with respect to increasing azimuth angle of the first acoustic lens. For instance, a single-phase acoustic transducer may transmit a first component of the ultrasound wave through the first acoustic lens at a first azimuth angle $\theta=\theta_1$ and the first acoustic lens may impart a first phase shift $L*\theta_1$ to the first component. L may be a nonzero integer defined by the varying longitudinal thickness of the first acoustic lens. The acoustic transducer may also transmit a second component of the ultrasound wave through the first acoustic lens at a second azimuth angle $\theta=\theta_2$ and the first acoustic lens may impart a second phase shift $L*\theta_2$ to the second component. In this way, a progressive phase shift is imparted to the ultrasound wave with respect to an azimuth angle of the acoustic transducer from which the various components of the acoustic wave are transmitted, resulting in the formation of the ultrasound intensity well. The diameter of the ultrasound intensity well may be increased by increasing the magnitude of L (e.g., by increasing the thickness of the first acoustic lens) and decreased by decreasing the magnitude of L (e.g., by decreasing the thickness of the first acoustic lens). In some examples, the first acoustic lens may also include an additional section with a curved surface configured to focus the various components of the ultrasound wave into a focal plane of the medium.

In another example, the progressive phase shift is imparted to the ultrasound wave via a second acoustic lens comprising p segments. Each of the p segments may have a varying longitudinal thickness that increases proportionally with respect to increasing azimuth angle of the segment. A single-phase acoustic transducer may transmit a first component of the ultrasound wave through the second acoustic lens at a first azimuth angle $\theta=\theta_3$. The second acoustic lens may impart a first phase shift $L*\theta_3$ to the first component. L may be an integer multiple of p. The acoustic transducer may also transmit a second component of the ultrasound wave through the second acoustic lens at a second azimuth angle $\theta=\theta_4$. The second acoustic lens may impart a second phase shift $L*\theta_4$ to the second component. In this way, a progressive phase shift is imparted to the ultrasound wave with respect to an azimuth angle of the acoustic transducer from which the various components of the acoustic wave are transmitted, resulting in the formation of the ultrasound intensity well. The diameter of the ultrasound intensity well may be increased by increasing the magnitude of L (e.g., increasing p, the number of segments of the second acoustic lens) and decreased by decreasing the magnitude of L (e.g., decreasing p). In some examples, the second acoustic lens may also include a second section with a curved surface configured to focus the various components of the ultrasound wave into the medium.

Referring now to the Figures, FIG. 1 illustrates an example acoustic transducer device 100 configured to move or confine an object 122 within a medium 116 by transmitting a focused ultrasound wave 114 into the medium 116. The device 100 may include a processor 102, data storage 104, an input/output interface 106, a sensor module 108, and an acoustic transducer 110, any or all of which may be communicatively coupled to each other via a system bus or another connection mechanism 111. In some examples, the device 100 may also include an acoustic lens 112 that is acoustically coupled to the acoustic transducer 110.

The processor 102 may include a general purpose processor and/or a special purpose processor configured to execute program instructions stored within data storage 104. In some examples, the processor 102 may be a multi-core processor comprised of one or more processing units configured to coordinate to execute instructions stored within data storage 104. In one example, by executing program instructions stored within data storage 104, the processor 102 may provide input signals or signal parameters to the acoustic transducer 110 for transmission, steering, and/or focusing of the ultrasound wave 114. In another example, the processor 102 may provide to the acoustic transducer 110, input signals or signal parameters based on input received via the input/output interface 106.

Data storage 104 may include one or more volatile, non-volatile, removable, and/or non-removable storage components. Data storage 104 may be a magnetic, optical, or flash storage medium, and may be integrated in whole or in part with the processor 102 or other portions of the device 100. Further, the data storage 104 may be a non-transitory computer-readable storage medium, having stored thereon program instructions that, when executed by the processor 102, cause the device 100 to perform any function described in this disclosure. Such program instructions may be part of a software application that can be executed in response to inputs received from the input/output interface 106, for instance. The data storage 104 may also store other types of information or data, such as those types described throughout this disclosure.

The input/output interface 106 may enable interaction with a user of the device 100, if applicable. The input/output interface 106 may include input components such as dials, buttons, a keyboard, a mouse, a keypad, or a touch-sensitive panel, and output components such as a display screen (which, for example, may be combined with a touch-sensitive panel), a sound speaker, and a haptic feedback system. In one example, the input/output interface 106 may receive input indicating (i) various parameters defining the ultrasound wave 114 and/or (ii) various parameters for steering or focusing the ultrasound wave 114 upon various portions of the medium 116.

In some examples, the input/output interface 106 may include a display screen for displaying images of the object 122 or other sensory data collected by the sensor module 108. Properly positioning the ultrasound wave 114 upon or near the object 122 will generally involve characterizing the size, shape, location, and/or consistency of the object 122. The display screen may display images of the object 122 that are captured by the sensor module 108. The displayed images of the object 122 may be used prior to transmission of the ultrasound wave 114, or could be used in a real-time manner by monitoring the position of the object 122 while the ultrasound wave 114 is being transmitted.

The sensor module 108 may include any known hardware and/or software configured to collect sensory data from the object 122 or the medium 116 prior to, during, or after transmission of the ultrasound wave 114. For example, the sensor module 108 may include an imaging system to capture an image of the object 122 and provide the captured image to the input/output interface 106 for display. The sensor module 108 may include an (additional) acoustic transducer configured to (i) generate ultrasound waves that are scattered and/or reflected by the object 122, (ii) detect the ultrasound waves reflected and/or scattered by the object 122, and (iii) generate an image of the object 122 using the detected ultrasound waves. In another example, the sensor module 108 may include a magnetic resonance imaging (MRI) system. Any known imaging technique capable of imaging an object located within a human subject or various other media 116 is contemplated herein.

In some examples, the sensor module 108 may be integrated with the acoustic transducer 110. For instance, a single acoustic transducer or transducer array may be used for both moving/confining the object 122 and for imaging of the object 122.

The acoustic transducer 110 may include a signal generator configured to receive data or signals from the processor 102 or input/output interface 106 that is representative of parameters for the ultrasound wave 114. For instance, the processor 102 may send, to the acoustic transducer 110, data representative of input received via the input/output interface 106. In another example, the received input may simply indicate one of several predetermined ultrasound wave transmission protocols represented by program instructions stored at data storage 104. Such data received by the acoustic transducer 110 may indicate various ultrasound parameters such as operating power of the acoustic transducer 110, power density of the ultrasound wave 114, oscillation frequency of the ultrasound wave 114, pulse duration of the ultrasound wave 114, duty cycle of the ultrasound wave 114, and a number of ultrasound pulses to be generated, for example. The received data may also indicate a trajectory, path, or sequence of locations of the medium 116 along which the object 122 is to be moved. In other examples, the path of the ultrasound wave 114 may be manually and/or mechanically directed. In some examples, the acoustic transducer 110 may include a signal amplifier used to generate the ultrasound wave 114 at a desired power.

The acoustic transducer 110 may include one or more piezoelectric transducer elements configured to transmit components of the ultrasound wave 114 in response to receiving respective input signals representing the components of the ultrasound wave 114. For example, the acoustic transducer 110 may include a phased array of transducer elements configured to electronically focus or steer the ultrasound wave 114 upon various portions of the medium 116 and/or the object 122. Each transducer element of the acoustic transducer 110 may receive its own independent input signal or data. The acoustic transducer 110 may also include one or more transducer elements having a radius of curvature corresponding to a focal plane of the ultrasound wave 114/medium 116. The acoustic transducer 110 may be configured to generate an ultrasound wave of oscillation frequency ranging from 20 kHz-10 MHz, but other examples are possible.

In another example, the acoustic transducer 110 includes only a single transducer element or is provided with only a single-phase input signal. Here, the acoustic transducer 110 may be acoustically coupled to the acoustic lens 112 to generate the ultrasound wave 114 having the progressive phase shift.

In some examples, the acoustic lens 112 may impart varying degrees of phase shift to various components of the ultrasound wave 114 based on the region through which the various components pass through the acoustic lens 112. The acoustic lens 112 may include any material that differs in sound speed from the medium 116. That is, acoustic waves (e.g., sound/ultrasound waves) may propagate at different respective speeds through the acoustic lens 112 and the medium 116. The acoustic lens 112 may be made of materials such as plastics, ceramics, and/or metals. In one example, the acoustic lens 112 includes a UV-cured photopolymer plastic Accura 60. The acoustic lens 112 may include other materials as well. Example acoustic lenses 300 and 400 are depicted respectively in FIGS. 3 and 4 and discussed in more detail below.

The medium 116 may include any medium that surrounds, contains, or contacts the object 122, such as intact tissue of a living human subject, dissected biological tissue, a liquid medium (e.g., water), a medium (e.g., agar) on a petri dish, a liquid medium on a microscope slide, or the like. Further examples of the medium 116 may include a urinary tract, a renal tract, a ureter, a bladder, a urethra, a prostate gland, a salivary gland, a gall bladder, a gall tract, a blood vessel, or an intestinal tract. In some examples, the medium 116 may surround or contact a portion of the acoustic lens 112 and be acoustically coupled to the acoustic lens 112. In other examples, the medium 116 may be directly acoustically coupled to the acoustic transducer 110.

The object 122 may include any object suitable for movement and/or confinement via interaction with the ultrasound wave 114. Some examples of the object 122 include: a kidney stone, a urinary tract stone, a ureter stone, a bladder stone, a urethra stone, a prostate stone, a salivary stone, a gallbladder stone, a gall stone, a bile duct, a blood clot, blood, mucous, fecal matter, cerumen, a calcification, a calcified plaque, an atherosclerotic plaque, uric acid, struvite, calcium oxalate monohydrate, cysteine, a tonsil stone, solid non-biological matter, an electronic component, biological tissue, or non-biological tissue.

The ultrasound intensity well 118 is formed by transmission of the ultrasound wave 114 into the medium 116. The ultrasound intensity well 118 represents a region of the medium 116 which exhibits a first range of acoustic pressure.

The surrounding region 120 represents a region of the medium 116 that surrounds the ultrasound intensity well 118 and which exhibits a second range of acoustic pressure that exceeds the first range of acoustic pressure. The absolute pressure values of the first and second ranges of pressure are not important.

Figure 2:
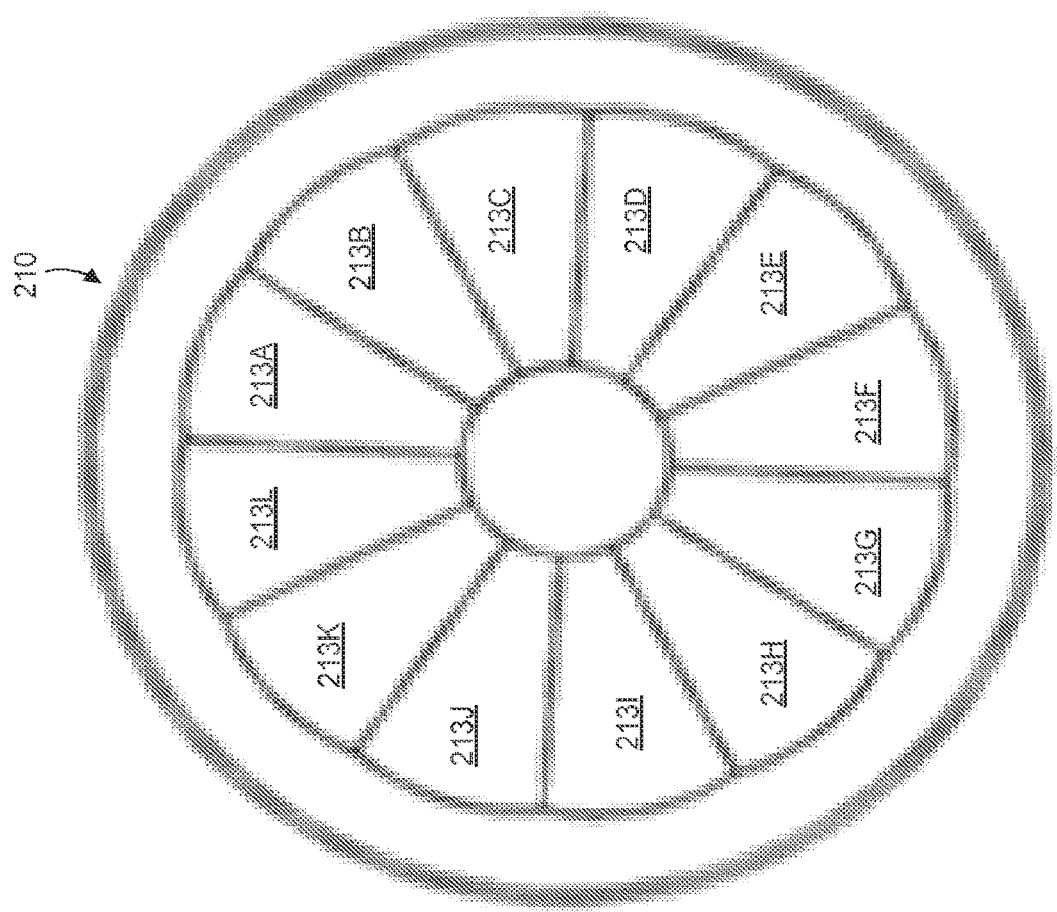
FIG. 2 shows an example acoustic transducer.

FIG. 2 is a detailed view of an acoustic transducer 210, including transducer elements 213A, 213B, 213C, 213D, 213E, 213F, 213G, 213H, 213I, 213J, 213K, and 213L. In some examples, the transducer elements 213A-L may be arranged and shaped (e.g., curved) so as to transmit an ultrasound wave that is focused at an axial distance of 75 mm from a center of the acoustic transducer 110. The acoustic transducer 110 may have (i) a central opening having a diameter of approximately 11 mm and (ii) an outer diameter of approximately 75 mm.

As described above with regard to FIG. 1, each of the transducer elements 213A-L may be configured to receive an independent input signal from a signal generator of the acoustic transducer 110, from the processor 102, or from the input/output interface 106. Each of the transducer elements 213A-L may be configured to vibrate at a frequency and a phase represented by the respective input signals received, thus transmitting the ultrasound wave 114.

In another example (not shown), the acoustic transducer 110 may include only a single-element transducer configured to transmit a single-phase ultrasound wave 114. In some cases, the single-element transducer may be curved so as to focus the ultrasound wave 114 upon a focal plane of the medium 116 that surrounds or contacts the object 122. In the case of the single-element transducer, it may be beneficial to acoustically couple the acoustic transducer 110 to an acoustic lens 300 or 400 of FIGS. 3 and 4 respectively, so that an azimuthally-dependent progressive phase shift may be imparted to the ultrasound wave 114 via the acoustic lens 300 or 400.

Figure 3:
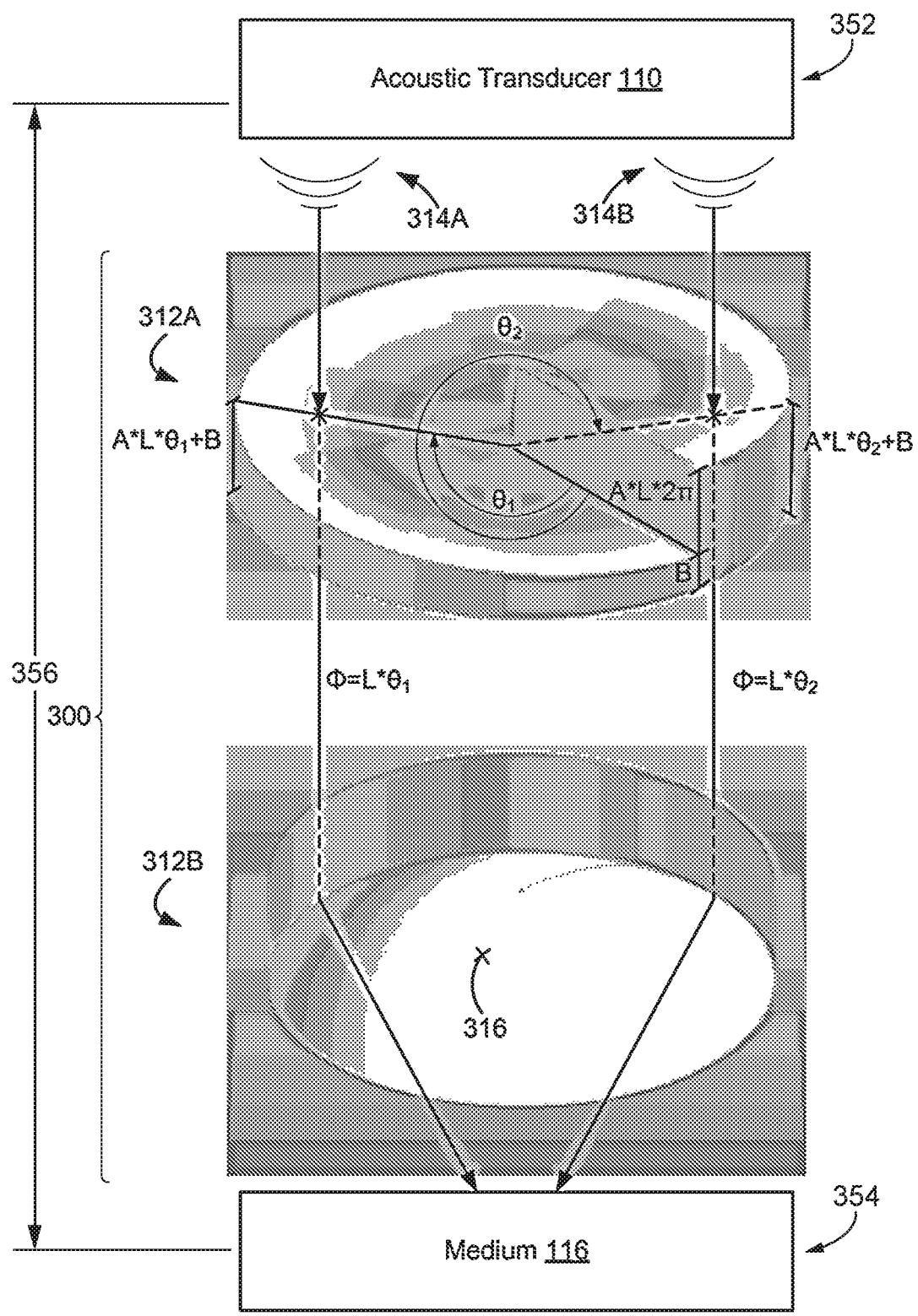
FIG. 3 shows an example acoustic lens configured for phase-shifting and focusing of components of an ultrasound wave.

FIG. 3 shows an example acoustic lens 300 configured for phase-shifting and/or focusing of components 314A and 314B of an ultrasound wave (e.g., ultrasound wave 114). As shown in FIG. 3, the acoustic transducer 110 is located in a first space 352 and the medium 116 is located in a second space 354. The first space 352 is axially offset by an axial offset 356 from the second space 354, where the ultrasound waves form the ultrasound intensity well. In various embodiments, the acoustic lens 300 may include one or both of the first section 312A and the second section 312B. In a first embodiment of the acoustic lens 300, only the first section 312A is acoustically coupled to the acoustic transducer 110. In a second embodiment of the acoustic lens 300, only the second section 312B is acoustically coupled to the acoustic transducer 110. In a third embodiment of the acoustic lens 300, the first section 312A is acoustically coupled to the acoustic transducer 110 and the second section 312B is acoustically coupled to the first section 312A. In a fourth embodiment of the acoustic lens 300, the second section 312B is acoustically coupled to the acoustic transducer 110 and the first section 312A is acoustically coupled to the second section 312B.

The first section 312A may have a varying longitudinal thickness (e.g., a thickness parallel to the propagation direction of components 314A and 314B). The varying longitudinal thickness may increase proportionally with respect to increasing azimuth angle of the acoustic lens 300. For example, the first section 312A may have a first longitudinal thickness $A*L*\theta_1+B$ at a first azimuth angle $\theta=\theta_1$, and a second longitudinal thickness $A*L*\theta_2+B$ at a second azimuth angle $\theta=\theta_2$. The first section 312A may also include a boundary at which the varying longitudinal thickness of the first section 312A discontinuously changes from $A*L*2\pi+B$ to B.

A and B may be nonzero positive numbers and L may be a nonzero integer. B may correspond to a minimum longitudinal thickness of the first section 312A at $\theta=0$ (i.e., $\theta=2\pi$). The value of L may correspond to a range of phase shifts that the first section 312A may impart to various components of an ultrasound wave that pass through the first section 312A. In some examples, L is equal to −6, −5, −4, −3, −2, −1, 1, 2, 3, 4, 5, or 6, corresponding to progressive phase shifts of −12π, −10π, −8π, −6π, −4π, −2π, 2π, 4π, 6π, 8π, 10π, and 12π across a full $\theta=2\pi$ sweep of the azimuth angle. The value of L may determine a diameter of the ultrasound intensity well 118. That is, the diameter of the ultrasound intensity well 118 may be proportional to the magnitude of L. Additionally, A may be defined by the equation $$A = \frac{\lambda_m}{2\pi(1-n)} \quad [1]$$

where $\lambda_m$ is greater than about 148.2 μm and less than about 74.1 mm (roughly corresponding to wavelengths of acoustic waves of frequency ranging from about 20 kHz to 10 MHz traveling through a water medium). More specifically, $\lambda_m$ may be about equal to 988 μm (roughly corresponding to a wavelength of an acoustic wave of frequency of about 1.5 MHz traveling through a water medium). In another example, $\lambda_m$ may be about equal to 4.49 mm (roughly corresponding to a wavelength of an acoustic wave of frequency of about 0.33 MHz traveling through a water medium). n may be an acoustic refractive index of the acoustic lens 300 relative to the medium 116. For example, if n=3, then acoustic waves would travel three times slower through the acoustic lens 300 than through the medium 116. In another example, if n=0.5, then acoustic waves would travel two times faster through the acoustic lens 300 than through the medium 116.

As shown in FIG. 3, a longitudinal thickness of the first section 312A may be substantially constant along a radial direction of the first section 312A of the acoustic lens 300.

The second section 312B may include a curved surface 316 configured to focus, upon a focal plane of the medium 116, components of an ultrasound wave received at respective azimuth angles of the acoustic lens 300.

Additional functional applications of the acoustic lens 300 will be discussed further below.

Figure 4:
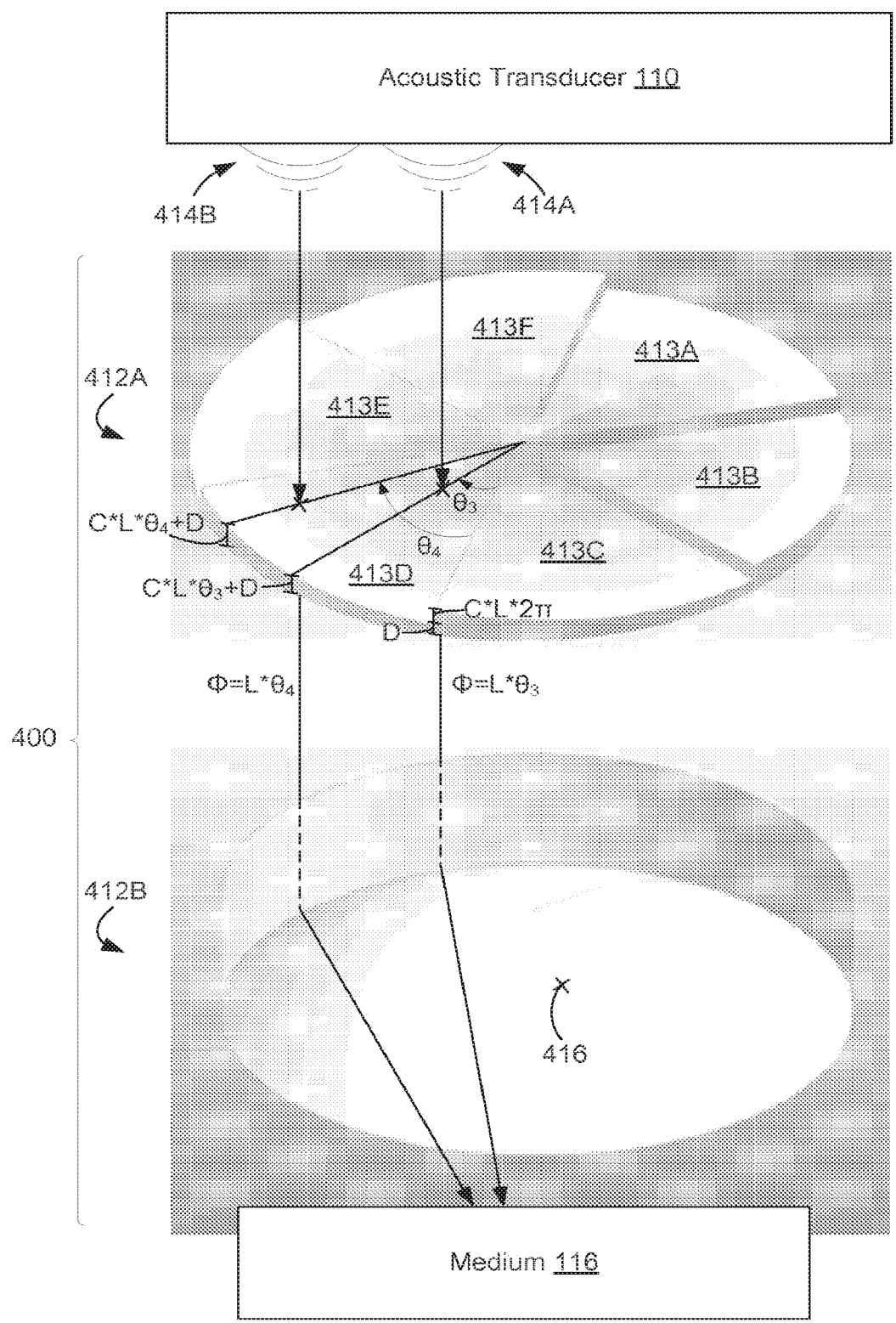
FIG. 4 shows another example acoustic lens configured for phase-shifting and focusing of components of an ultrasound wave.

FIG. 4 shows an example acoustic lens 400 configured for phase-shifting and focusing of components 414A and 414B of an ultrasound wave (e.g., ultrasound wave 114). In various embodiments, the acoustic lens 400 may include one or both of the first section 412A and the second section 412B. In a first embodiment of the acoustic lens 400, only the first section 412A is acoustically coupled to the acoustic transducer 110. In a second embodiment of the acoustic lens 400, only the second section 412B is acoustically coupled to the acoustic transducer 110. In a third embodiment of the acoustic lens 400, the first section 412A is acoustically coupled to the acoustic transducer 110 and the second section 412B is acoustically coupled to the first section 412A. In a fourth embodiment of the acoustic lens 400, the second section 412B is acoustically coupled to the acoustic transducer 110 and the first section 412A is acoustically coupled to the second section 412B.

The first section 412A may include a plurality of segments 413A, 413B, 413C, 413D, 413E, and 413F. Each of the plurality of segments 413A-F may have a varying longitudinal thickness that increases proportionally with respect to increasing azimuth angle of the segment. For example, the segment 413D may have a first longitudinal thickness $C*L*\theta_3+D$ at a first azimuth angle $\theta=\theta_3$, and a second longitudinal thickness $C*L*\theta_4+D$ at a second azimuth angle $\theta=\theta_4$. The first section 412A may include a boundary between the segment 413D and the segment 413C at which a longitudinal thickness of the first section 412A changes from $C*L*(\pi/3)+D$ to D (for the case where L=6). In the case of a generalized first section 412A having p segments, the first section 412A may include a boundary between adjacent segments at which a longitudinal thickness of the first section 412A changes from $C*L*(2\pi/p)+D$ to D.

C and D may be nonzero positive numbers and L may be an integer multiple of p (an integer multiple of 6 in the case of the first section 412A). D may correspond to a minimum longitudinal thickness of the segment 413D at $\theta=0$. In some examples, L is equal to −6, −5, −4, −3, −2, 2, 3, 4, 5, or 6. In the example depicted in FIG. 4, p is equal to 6, so L may be equal to integer multiples of 6, respectively corresponding to phase shift ranges of (+/−)2π, (+/−)4π, (+/−)6π, etc. across a full π/3 sweep of an azimuth angle of the segment 413D. In the generalized case of p segments, a total range of phase shift imparted to the ultrasound wave by a given segment may be equal to 2πL/p. In some examples, L may be equal to the number of segments of the first section 412A (e.g. L=p=6). The value of L may determine a diameter of the ultrasound intensity well 118. That is, the diameter of the ultrasound intensity well 118 may be proportional to the magnitude of L. Additionally, C may be defined by the equation $$C = \frac{\lambda_m}{2\pi(1-n)} \quad [2]$$

where $\lambda_m$ is greater than about 148.2 μm and less than about 74.1 mm (roughly corresponding to wavelengths of acoustic waves of frequency ranging from about 20 kHz to 10 MHz traveling through a water medium). More specifically, $\lambda_m$ may be about equal to 988 μm (roughly corresponding to a wavelength of an acoustic wave of frequency of about 1.5 MHz traveling through a water medium). In another example, $\lambda_m$ may be about equal to 4.49 mm (roughly corresponding to a wavelength of an acoustic wave of frequency of about 0.33 MHz traveling through a water medium). n may be an acoustic refractive index of the acoustic lens 400 relative to the medium 116. For example, if n=3, then acoustic waves would travel three times slower through the acoustic lens 400 than through the medium 116. In another example, if n=0.5, then acoustic waves would travel two times faster through the acoustic lens 400 than through the medium 116.

As shown in FIG. 4, a longitudinal thickness of the first section 412A may be substantially constant along a radial direction of the first section 412A.

The second section 412B may include a curved surface 416 configured to focus, upon a focal plane of the medium 116, components of an ultrasound wave received at respective azimuth angles of the acoustic lens 400.

Additional functional applications of the acoustic lens 400 will be discussed further below.

Figure 5:
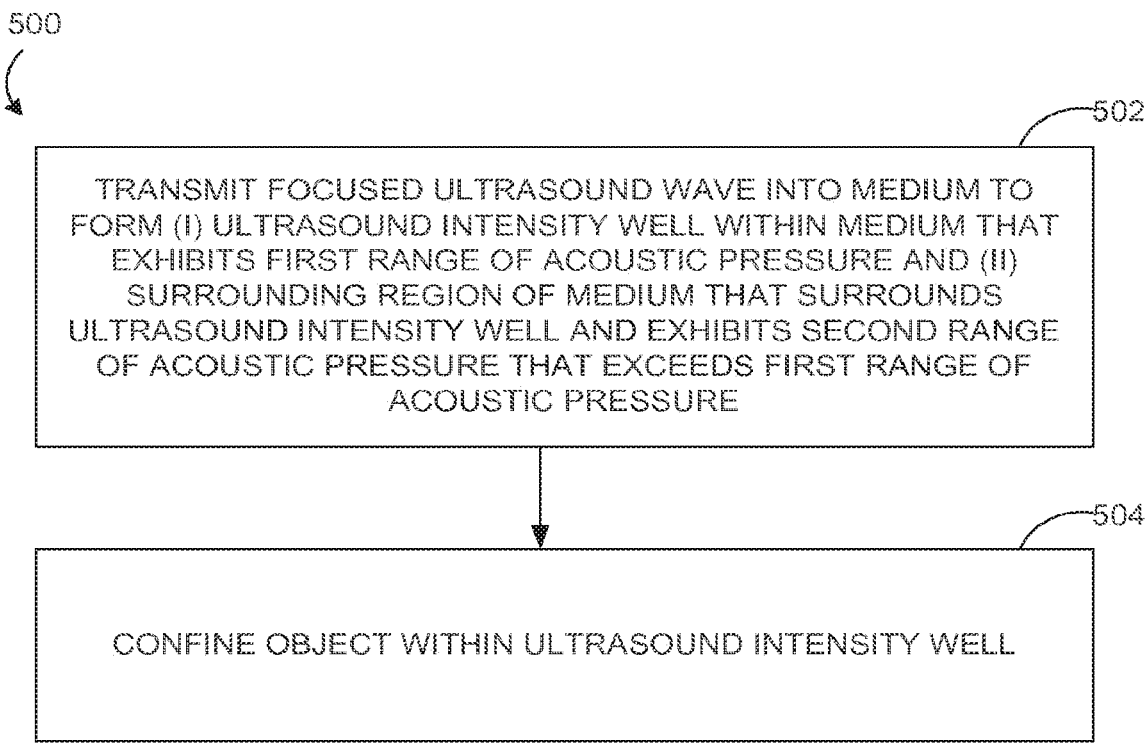
FIG. 5 is a block diagram depicting an example method for confining or moving an object using an ultrasound wave.

FIG. 5 is a flow chart depicting an example method 500 for confining or moving an object using an ultrasound wave. Method 500 shown in FIG. 5 presents an example method that can be implemented within an operating environment including, for example, the acoustic transducer device 100, the acoustic transducer 110, the acoustic lens 112, the medium 116, the object 122, the acoustic lens 300, and the acoustic lens 400. Method 500 may include one or more operations, functions, or actions as illustrated by one or more of blocks 502 and 504. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

In addition, for the methods 500 and other processes and methods disclosed herein, the flowcharts show functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer-readable medium, for example, such as a storage device including a disk(s) or hard drive(s). In some embodiments, the program code may be stored in memory (e.g., disks or disk arrays) associated with and/or connected to a server system that makes the program code available for download to desktop/laptop computers, smart phones, tablet computers, or other types of computing devices. The computer-readable medium may include non-transitory computer-readable media, for example, such as computer-readable media that stores data for short periods of time like register memory, processor cache, and Random Access Memory (RAM). The computer-readable medium may also include non-transitory media, such as secondary or persistent long-term storage, like read-only memory (ROM), optical or magnetic disks, compact-disc read-only memory (CD-ROM), for example. The computer-readable media may also be any other volatile or non-volatile storage systems. The computer-readable medium may be considered a computer-readable storage medium, for example, or a tangible storage device. In addition, for the method 500 and other processes and methods disclosed herein, each block in FIG. 5 may represent circuitry that is wired to perform the specific logical functions in the process.

At block 502, the method 500 includes transmitting a focused ultrasound wave into a medium to form (i) an ultrasound intensity well within the medium that exhibits a first range of acoustic pressure and (ii) a surrounding region of the medium that surrounds the ultrasound intensity well and exhibits a second range of acoustic pressure that exceeds the first range of acoustic pressure.

As shown in FIG. 1, the acoustic transducer 110 may transmit the ultrasound wave 114 into the medium 116 to form the ultrasound intensity well 118 within the medium 116. In order to transmit the ultrasound wave 114, the acoustic transducer 110 may receive an input voltage ranging from 90-100 V and a time-averaged power of 2.25 W, but other examples are possible. The ultrasound intensity well 118 may exhibit a first range of acoustic pressure (discussed in more detail below). The ultrasound wave 114 may also form the surrounding region 120 within the medium 116 that exhibits a second range of acoustic pressure that exceeds the first range of acoustic pressure (discussed in more detail below).

Figure 6:
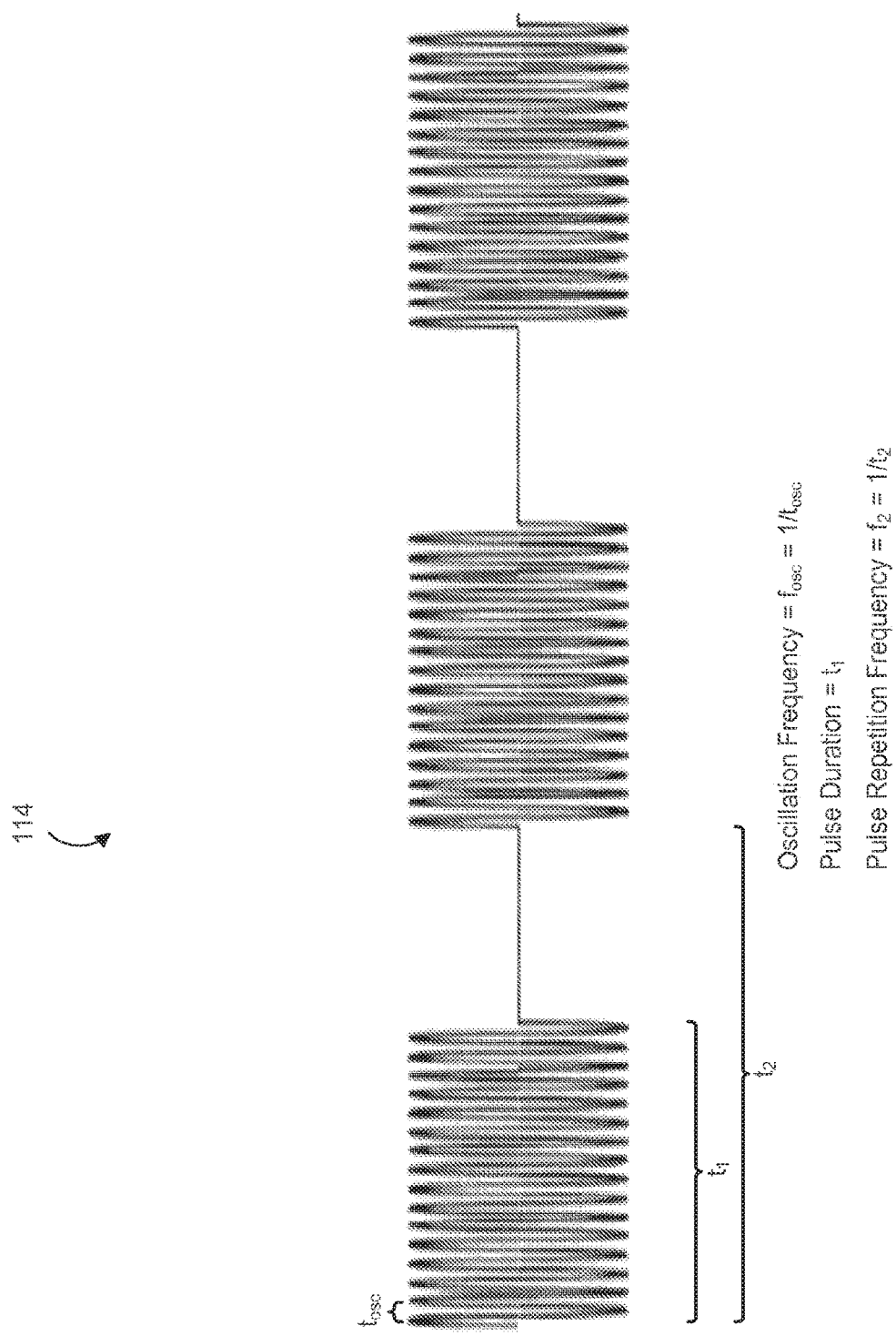
FIG. 6 shows an example ultrasound wave.

FIG. 6 shows an example ultrasound wave 114 transmitted by the acoustic transducer 110. The ultrasound wave 114 may have an oscillation frequency $f_{osc}$ ranging from 20 kHz to 10 MHz (e.g., 1.5 MHz or 0.33 MHz). The ultrasound wave 114 may have a pulse repetition frequency $f_2$ of about 100 Hz and a pulse duration ti of about 33.3 μs. Other examples are possible as well.

Transmitting the ultrasound wave may include each transducer element of an array of m transducer elements transmitting a respective component of the ultrasound wave that is phase shifted by $2\pi L/m$ radians with respect to a component of the ultrasound wave transmitted by an adjacent transducer element. L may be any nonzero integer (e.g., −6, −5, −4, −3, −2, −1, 1, 2, 3, 4, 5, or 6) and m may be greater than or equal to 3 (e.g., m=12). Other examples are possible.

For instance, the transducer elements 213A-L may each transmit a component of the ultrasound wave 114 with respective phase shifts according to the table below.

| Transducer Element | Phase Shift |
| --- | --- |
| 213A | 0 |
| 213B | $\pi L/6$ |
| 213C | $\pi L/3$ |
| 213D | $\pi L/2$ |
| 213E | $2\pi L/3$ |
| 213F | $5\pi L/6$ |
| 213G | $\pi L$ |
| 213H | $7\pi L/6$ |
| 213I | $4\pi L/3$ |
| 213J | $3\pi L/2$ |
| 213K | $5\pi L/3$ |
| 213L | $11\pi L/6$ |

Transmitting the ultrasound wave 114 with such varying degrees of phase shift may form the ultrasound intensity well 118 and the surrounding region 120.

In another example, an acoustic transducer 110 may transmit a first component 314A and a second component 314B of the ultrasound wave 114. In this example, the first component 314A and the second component 314B (as transmitted by the acoustic transducer 110) might have no phase shift relative to each other. The acoustic transducer 110 may transmit the first component 314A through the first section 312A at a first azimuth angle $\theta=\theta_1$. The first section 312A may impart a first phase shift $L*\theta_1$ to the first component 314A. L may be any nonzero integer (e.g., −6, −5, −4, −3, −2, −1, 1, 2, 3, 4, 5, or 6). The acoustic transducer 110 may also transmit the second component 314B through the first section 312A at a second azimuth angle $\theta=\theta_2$. The first section 312A may impart a second phase shift $L*\theta_2$ to the second component 314B.

At the first azimuth angle $\theta=\theta_1$, the first section 312A may have a first longitudinal thickness $A*L*\theta_1+B$, and at the second azimuth angle $\theta=\theta_2$ the first section 312A may have a second longitudinal thickness $A*L*\theta_2+B$. A may be defined by $$A = \frac{1}{2\pi\left(\frac{1}{\lambda_m} - \frac{1}{\lambda_p}\right)} \quad [3]$$

where $\lambda_m$ is a wavelength of the ultrasound wave 114 propagating through the medium 116, and $\lambda_p$ is a wavelength of the ultrasound wave 114 propagating through the acoustic lens 300.

After the first component 314A passes through the first section 312A, the first component 314A may be transmitted through the second section 312B. A curved surface 316 of the second section 312B may focus the first component 314A upon a focal plane of the medium 116.

After the second component 314B passes through the first section 312A, the second component 314B may be transmitted through the second section 312B. The curved surface 316 of the second section 312B may focus the second component 314B upon the focal plane of the medium 116.

In other examples, the acoustic lens 300 may be configured such that the components 314A and 314B of the ultrasound wave 114 may first pass through the second section 312B to be focused and then pass through the first section 312A to have the respective phase shifts applied.

FIGS. 7A-F show measured pressure amplitudes within a focal plane of a medium 716 for various values of L. FIG. 7A shows an ultrasound intensity well 718A surrounded by a surrounding region 720A formed by an ultrasound wave corresponding to L=1. As shown, the diameter of the ultrasound intensity well 718A was on the order of a few tenths of a millimeter and the diameter of the surrounding region 720A was approximately 2.25 mm. The ultrasound intensity well 718A exhibited a first range of acoustic pressure of approximately 0-0.3 MPa and the surrounding region 720A exhibited a second range of acoustic pressure of approximately 0.3-0.7 MPa.

FIG. 7B shows an ultrasound intensity well 718B surrounded by a surrounding region 720B of a medium 716 formed by an ultrasound wave corresponding to L=3. As shown, the diameter of the ultrasound intensity well 718B was about 2 mm and the diameter of the surrounding region 720B was approximately 4.5 mm. The ultrasound intensity well 718B exhibited a first range of acoustic pressure of approximately 0-0.3 MPa and the surrounding region 720B exhibited a second range of acoustic pressure of approximately 0.3-0.4 MPa.

FIG. 7C shows an ultrasound intensity well 718C surrounded by a surrounding region 720C of a medium 716 formed by an ultrasound wave corresponding to L=4. As shown, the diameter of the ultrasound intensity well 718C was about 2.25 mm and the diameter of the surrounding region 720C was approximately 5.5 mm. The ultrasound intensity well 718C exhibited a first range of acoustic pressure of approximately 0-0.15 MPa and the surrounding region 720C exhibited a second range of acoustic pressure of approximately 0.15-0.35 MPa.

FIG. 7D shows an ultrasound intensity well 718D surrounded by a surrounding region 720D of a medium 716 formed by an ultrasound wave corresponding to L=5. As shown, the diameter of the ultrasound intensity well 718D was about 3.25 mm and the diameter of the surrounding region 720D was approximately 8.5 mm. The ultrasound intensity well 718D exhibited a first range of acoustic pressure of approximately 0-0.2 MPa and the surrounding region 720D exhibited a second range of acoustic pressure of approximately 0.2-0.4 MPa.

FIG. 7E shows an ultrasound intensity well 718E surrounded by a surrounding region 720E of a medium 716 formed by an ultrasound wave corresponding to L=6. As shown, the diameter of the ultrasound intensity well 718E was about 3.5 mm and the diameter of the surrounding region 720E was approximately 8.5 mm. The ultrasound intensity well 718E exhibited a first range of acoustic pressure of approximately 0-0.2 MPa and the surrounding region 720E exhibited a second range of acoustic pressure of approximately 0.2-0.4 MPa.

In another example, transmitting the ultrasound wave into the medium may include transmitting a first component of the ultrasound wave through an acoustic lens comprising p segments, where p is greater than or equal to 2. The first component may be transmitted through the acoustic lens at a first azimuth angle $\theta=\theta_3$ and the acoustic lens may impart a first phase shift $L*\theta_3$ to the first component. L may be an integer multiple of p (or perhaps equal to p). Transmitting the ultrasound wave into the medium may also include transmitting a second component of the ultrasound wave through the acoustic lens at a second azimuth angle $\theta=\theta_4$. The acoustic lens may impart a second phase shift $L*\theta_4$ to the second component.

Referring to FIG. 4 for example, the acoustic transducer 110 may transmit a first component 414A of the ultrasound wave 114 through the segment 413D of the first section 412A at a first azimuth angle $\theta=\theta_3$. The first section 412A may impart a first phase shift $L*\theta_3$ to the first component 414A. L may be an integer multiple of p, or in some cases L may be equal to p. L may take on values such as −6, −5, −4, −3, −2, −1, 1, 2, 3, 4, 5, or 6. In the example depicted in FIG. 4, p=6 (corresponding to segments 413A-F). The acoustic transducer 110 may also transmit a second component 414B of the ultrasound wave 114 through the segment 413D of the first section 412A at a second azimuth angle $\theta=\theta_4$. The first section 412A may impart a second phase shift $L*\theta_4$ to the second component 414B.

After the first component 414A passes through the first section 412A, the first component 414A may be transmitted through the second section 412B. A curved surface 416 of the second section 412B may focus the first component 414A upon a focal plane of the medium 116.

After the second component 414B passes through the first section 412A, the second component 414B may be transmitted through the second section 412B. The curved surface 416 of the second section 412B may focus the second component 414B upon the focal plane of the medium 116.

In other examples, the acoustic lens 400 may be configured such that the components 414A and 414B of the ultrasound wave 114 may first pass through the second section 412B to be focused and then pass through the first section 412A to have the respective phase shifts applied.

At the first azimuth angle $\theta=\theta_3$ the first section 412A may have a first longitudinal thickness $C*L*\theta_3+D$, where C and D are nonzero positive numbers. At the second azimuth angle $\theta=\theta_4$ the first section 412A may have a second longitudinal thickness $C*L*\theta_4+D$. C may be defined by $$C = \frac{1}{2\pi\left(\frac{1}{\lambda_m} - \frac{1}{\lambda_p}\right)} \quad [4]$$

where $\lambda_m$ is a wavelength of the ultrasound wave 114 propagating through the medium 116, and $\lambda_p$ is a wavelength of the ultrasound wave 114 propagating through the acoustic lens 400.

Regardless of whether the ultrasound wave 114 is focused using the acoustic transducer 210 or using the acoustic lens 300 or 400, the ultrasound wave 114 may be focused at a focal plane of the medium 116. This may result in the formation of the ultrasound intensity well 118 within the focal plane and a surrounding region 120 that has an annular shape within the focal plane. The ultrasound wave 114 may be focused upon a focal point (e.g., a center point) within the ultrasound intensity well 118. The focal point may exhibit a local minimum of acoustic pressure within the focal plane.

Figure 8:
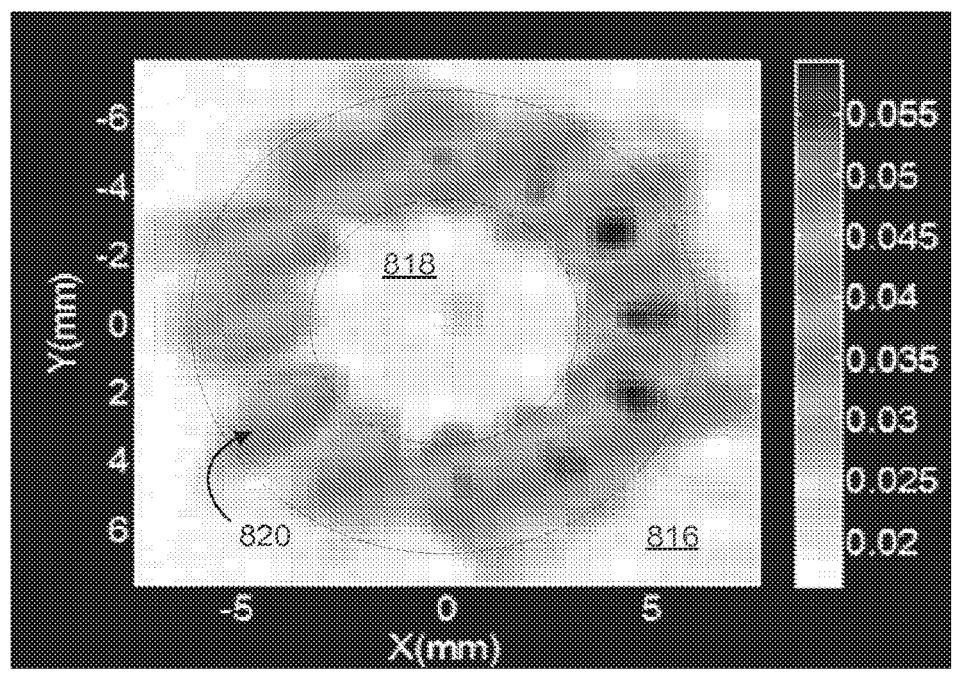
FIG. 8 shows the effect of an example acoustic lens upon measured pressure amplitudes within a focal plane of a medium.

FIG. 8 shows the effect of an example acoustic lens 400 upon measured pressure amplitude within a focal plane of a medium 116. FIG. 8 shows an ultrasound intensity well 818 surrounded by a surrounding region 820 of a medium 816 formed by an ultrasound wave. As shown, the diameter of the ultrasound intensity well 818 was about 7 mm and the diameter of the surrounding region 820 was approximately 13 mm. The ultrasound intensity well 818 exhibited a first range of acoustic pressure of approximately 0-0.035 MPa and the surrounding region 820 exhibited a second range of acoustic pressure of approximately 0.035-0.06 MPa.

Figure 9A:
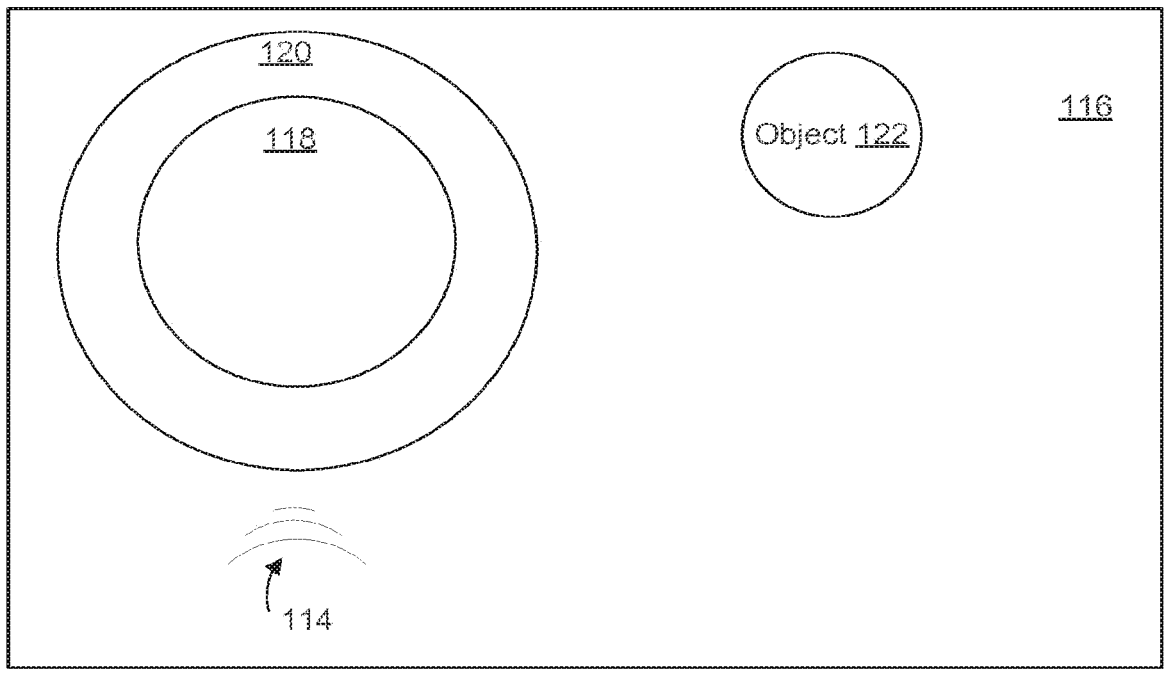
FIGS. 9A, 9B, 9C, and 9D show confinement or movement of an object using an ultrasound wave.

At block 504, the method 500 includes confining an object within the ultrasound intensity well. As shown in FIG. 9A, an ultrasound intensity well 118 and a surrounding region 120 is formed within the medium 116 via transmission of an ultrasound wave by an acoustic transducer. In the example of FIG. 9A, the ultrasound intensity well 118 and the surrounding region 120 are formed away from the location of the object 122 within the medium 116.

Figure 9B:
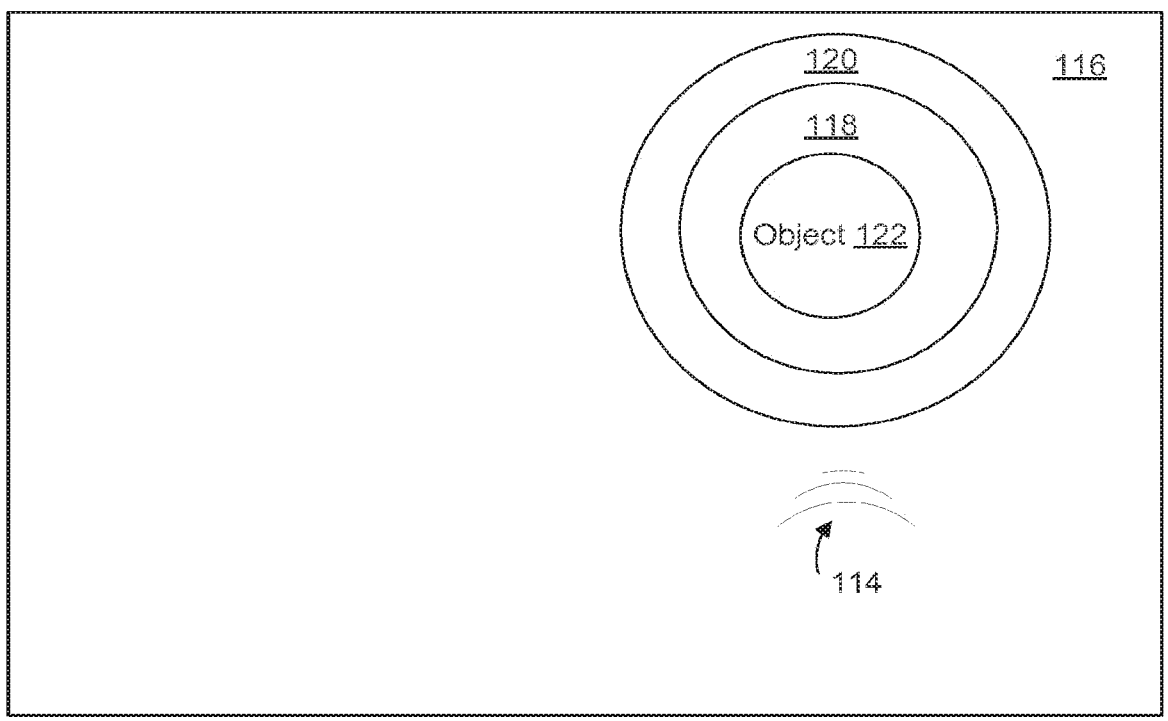

In FIG. 9B, the ultrasound intensity well 118 and the surrounding region 120 has been electronically or mechanically steered so that the ultrasound intensity well 118 surrounds the object 122. In another example, FIG. 9B depicts formation of the ultrasound intensity well 118 and the surrounding region 120 around the object 122, instead of formation of the ultrasound intensity well 118 and the surrounding region 120 away from the object 122 followed by steering of the ultrasound intensity well 118 and the surrounding region 120 toward the object 122.

Figure 9C:
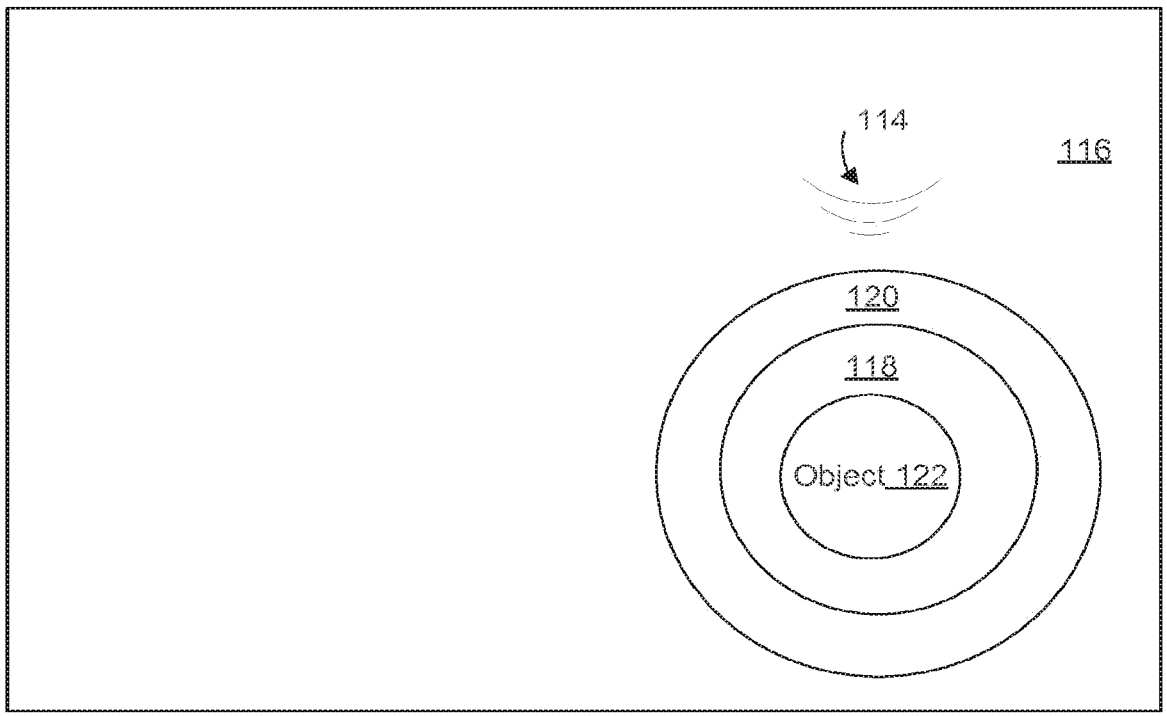

When compared to FIG. 9B, in FIG. 9C the ultrasound intensity well 118 and the surrounding region 120 have been steered downward, moving the object 122 downward as well. The downward direction depicted in FIGS. 9B and 9C may be normal to the direction of propagation of the ultrasound wave 114. That is, steering of the ultrasound wave 114 may cause movement of the object 122 in directions substantially parallel to the focal plane of the medium 116 (i.e., directions normal to the direction of propagation of the ultrasound wave 114).

Figure 9D:
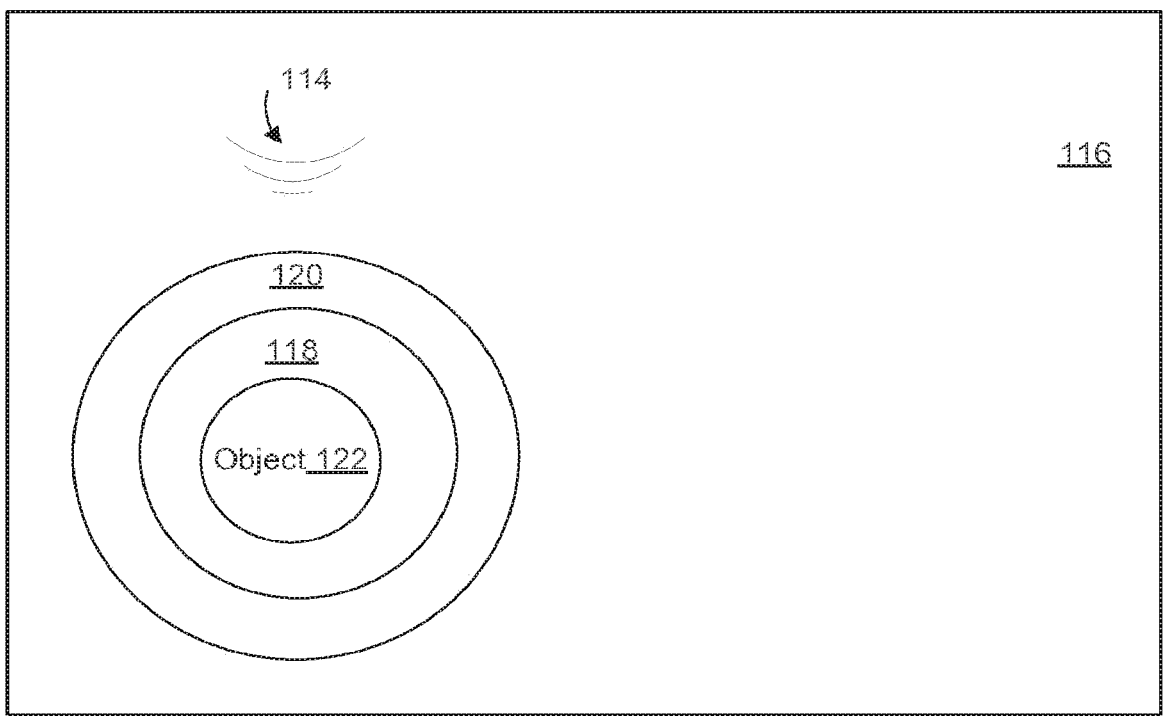

When compared to FIG. 9C, in FIG. 9D the ultrasound intensity well 118 and the surrounding region 120 have been steered leftward, moving the object 122 leftward as well. The leftward direction depicted in FIGS. 8C and 8D may be normal to the direction of propagation of the ultrasound wave 114.

As mentioned previously, the ultrasound wave 114 may be focused at a focal plane of the medium 116. The object 122 may be confined or moved by an acoustic pressure gradient directed toward the ultrasound intensity well 118 from the surrounding region 120 of the medium 116.

In examples where the ultrasound wave 114 is transmitted by an acoustic transducer comprising one or more transducer elements (e.g., acoustic transducer 210 of FIG. 2), steering the ultrasound wave 114 so that the object 122 is within the ultrasound intensity well 118 may include adjusting input signals provided respectively to the one or more transducer elements, as is known in the art. This may include situations where the ultrasound wave 114 is steered to move the object 122 in directions parallel to the focal plane of the medium 116.

In other examples, steering the ultrasound wave 114 so that the object 122 is within the ultrasound intensity well 118 may include mechanically adjusting the acoustic transducer 110, as is known in the art. This may include situations where the ultrasound wave 114 is steered to move the object 122 in directions parallel to the focal plane of the medium 116.

FIG. 10 shows rotation of an object 122 via a mechanical torque 123 provided by an ultrasound wave 114. The mechanical torque 123 may be a product of a rotational pressure gradient exhibited by the surrounding region 120 formed by the ultrasound wave 114. For example, the progressive phase shift imparted to the ultrasound wave 114 by either the acoustic transducer 210, the acoustic lens 300, or the acoustic lens 400 may generate the rotational pressure gradient and apply the mechanical torque 123 to the object 122. The object 122 may vibrate and/or move about the ultrasound intensity well 118 and contact an inner edge of the surrounding region 120 from time to time, causing rotation of the object 122 via the mechanical torque 123 as shown in FIG. 10. Although in FIG. 10 rotation of the object 122 is shown in the clockwise direction, counterclockwise rotation with respect to the focal plane of the medium 116 is also possible.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

The invention claimed is:

1. A device for treating an object in a body, comprising:
a phased array acoustic transducer comprising a plurality of transducer elements arranged in a first space;
one or more processors; and
a computer-readable medium storing instructions that, when executed by the one or more processors, cause the acoustic transducer to perform functions comprising:
transmitting an ultrasound wave axially away from a first space and into a medium to form (i) an ultrasound intensity well in a second space within the medium that exhibits a first range of acoustic pressure and (ii) a surrounding region in the second space of the medium that surrounds the ultrasound intensity well and exhibits a second range of acoustic pressure that exceeds the first range of acoustic pressure, wherein the second space is axially offset from the first space; and
treating the object by the ultrasound intensity well.

2. The device of claim 1, wherein the computer-readable medium includes further instructions to cause the acoustic transducer to perform the function of moving the object by moving the ultrasound intensity well.

3. The device of claim 1, wherein the computer-readable medium includes further instructions to cause the acoustic transducer to perform the function of confining the object.

4. The device of claim 1, and wherein the plurality of transducer elements are circumferentially arranged about the central opening.

5. The device of claim 4, wherein the acoustic transducer comprises a central opening.

6. The device of claim 5, wherein the central opening has a diameter of about 11 mm.

7. The device of claim 4, wherein the acoustic transducer has a diameter of about 75 mm.

8. The device of claim 4, wherein the plurality of transducer elements includes m elements, and wherein each of the transducer elements transmits a component of the ultrasound wave that is phase shifted by $2\pi L/m$ radians with respect to an adjacent transducer element, where L is a nonzero integer.

9. The device of claim 1, wherein the acoustic transducer is configured to emit the ultrasound wave at a frequency between 20 kHz and 10 MHz.

10. The device of claim 1, wherein the intensity well has a circular shape.

11. The device of claim 1, wherein the first range of acoustic pressure corresponds to 0-0.3 MPa, and wherein the second range of acoustic pressure corresponds to 0.3-0.7 MPa.

12. The device of claim 1, wherein the device further comprises a lens configured for transmitting the ultrasound wave, and wherein a thickness of the lens is uneven in a direction of the ultrasound wave.

13. The device of claim 1, wherein transmitting the ultrasound wave comprises:
transmitting a first component of the ultrasound wave through an acoustic lens at a first azimuth angle $\theta=\theta_1$, wherein the acoustic lens imparts a first phase shift $L*\theta_1$ to the first component, wherein L is a nonzero integer; and
transmitting a second component of the ultrasound wave through the acoustic lens at a second azimuth angle $\theta=\theta_2$, wherein the acoustic lens imparts a second phase shift $L*\theta_2$ to the second component.

14. The device of claim 13, wherein the acoustic lens has a varying longitudinal thickness that increases proportionally with respect to increasing azimuth angle of the acoustic lens.

15. The device of claim 13,
wherein at the first azimuth angle $\theta=\theta_1$ the acoustic lens has a first longitudinal thickness $A*L*\theta_1+B$, wherein A and B are nonzero positive numbers, and
wherein at the second azimuth angle $\theta=\theta_2$ the acoustic lens has a second longitudinal thickness $A*L*\theta_2+B$.

16. A method for treating an object in a body, comprising:
emitting an ultrasound wave by a phased array acoustic transducer comprising a plurality of transducer elements arranged in a first space;
transmitting the ultrasound wave axially away from the first space and into a medium;
forming (i) an ultrasound intensity well in a second space within the medium that exhibits a first range of acoustic pressure, wherein the second space is axially offset from the first space;
forming (ii) a surrounding region in the second space of the medium that surrounds the ultrasound intensity well and exhibits a second range of acoustic pressure that exceeds the first range of acoustic pressure; and
treating the object by the ultrasound intensity well.

17. The method of claim 16, further comprising moving the object by moving the ultrasound intensity well.

18. The method of claim 16, further comprising confining the object by the ultrasound intensity well.

19. The method of claim 16, and wherein the plurality of transducer elements are circumferentially arranged about the central opening.

20. The method of claim 16, wherein the acoustic transducer is configured to emit the ultrasound wave at a frequency between 20 kHz and 10 MHz.

21. The method of claim 16, wherein the acoustic transducer is configured to emit the ultrasound wave at a frequency of about 1.5 MHz.

22. The method of claim 16, wherein the first range of acoustic pressure corresponds to 0-0.3 MPa, and wherein the second range of acoustic pressure corresponds to 0.3-0.7 MPa.

* * * * *